US00PP08996P

United States Patent [19]

Bak et al.

[11] Patent Number: Plant 8,996

[45] Date of Patent: Nov. 29, 1994

[54] GUZMANIA PLANT NAMED PAX

[75] Inventors: Gerardus J. Bak, Assendelft; Nicolaas D. Steur, Oude Niedorp; Elly Bak, Rijsenhout, all of Netherlands

[73] Assignee: Corn, Bak B.V., Assendelft, Netherlands

[21] Appl. No.: 183,041

[22] Filed: Jan. 18, 1994

[51] Int. Cl.[5] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Foley & Lardner

[57] ABSTRACT

A new cultivar of Guzmania named Pax, characterized by its superior floral bract production, cream-white inflorescence, star-shaped inflorescence and individual flowers only in the middle part of the inflorescence.

3 Drawing Sheets

The present invention relates to a new and distinct cultivar of Guzmania, hereinafter referred to by the cultivar name Pax. Guzmania comprise a genus within the family Bromeliaceae. The new cultivar is a hybrid resulting from a cross of unnamed parent plants identified below.

Guzmania comprise a genus of over 100 species of evergreen perennials suitable for cultivation in the home or under glass. Guzmania are predominantly epiphytic with a few terrestrial species and are native to the tropics. For the most part the species vary in diameter from 7 to 8 inches to 3 or 4 feet and have rosettes of glossy, smooth edged leaves.

Floral bracts of Guzmania frequently have brilliant colors and may last for many months. The range of flower colors for Guzmania varies considerably but is generally in the orange, red and red-purple ranges. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period, the central vase-like part of the lead rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

The new cultivar Pax is a product of a planned breeding program and was originated by the inventors from a cross made during such a program in Assendelft, The Netherlands, in 1983. The male, or pollen parent, was an in-breeding selection of a Guzmania hybrid identified by Code Number 8326010. The female, or seed parent, was a mutant of another unnamed Guzmania hybrid, identified by the Code Number 8326001.

The selection comprising the new variety was chosen after commencement of flowering of the progeny in 1986, and subsequent asexual propagation by offshoots and tissue culture at the above identified Assendelft location, has demonstrated that the combination of characteristics as herein disclosed for the new cultivar Pax are firmly fixed and are retained through successive generations of asexual reproduction.

Pax is particularly characterized by the following:

1. Superior floral bract production.
2. Cream-white inflorescence.
3. Star-shaped inflorescence.
4. Individual flowers only in the middle part of the inflorescence.

The closest comparison cultivar is Guzmania Grand Prix. Most of the characteristics described below for Pax, except for the color, size and shape of the inflorescence, are generally similar to those same characteristics of Grand Prix. Whereas the floral bract color of Grand Prix is red, the bract color of Pax is cream-white. The Pax inflorescence is smaller than Grand Prix. The Grand Prix inflorescence is compound whereas the Pax inflorescence is single.

Pax has not been tested under all available environmental conditions. The phenotype may slightly vary with variations in environmental conditions such as temperature, light intensity, day length and humidity, as is well understood by those skilled in the art, without, however, any variance in genotype.

The accompanying color photographic drawings show typical characteristics of Pax.

Sheet 1 comprises a top perspective view of a full plant with floral bracts and foliage.

Sheet 2 is a side view showing foliage and inflorescence of a specimen plant.

Sheet 3 is a more enlarged showing of the floral bracts and inflorescence.

In the following description, color references are made to The Royal Horticultural Society Color Chart (R.H.S.).

The following traits have been repeatedly observed and in combination distinguish Pax as a new and distinct cultivar. These observations, measurements and descriptions have been performed under greenhouse conditions in Assendelft, The Netherlands.

I. Plant:

*Form.*—Funnel form rosette.

*Height.*—Approximately 32–36 cm high when flowering.

*Growth habit.*—Stemless.

*Diameter.*—Approximately 50 cm at the time of flowering.

II. Foliage:

*Size of leaf.*—Approximately 24 to 34 cm long, and 2 to 3 cm wide.

*Shape of leaf.*—Linear lanceolate.

*Surface texture.*—Smooth.

*Variegation.*—None.

*Color.*—Upperside 147A. Underside: 137A. The color of leaves can change depending upon fertilization, light conditions and other environmental factors.

III. Bracts:

*Length.*—Scape bracts: Lowest approximately 23 cm and those just below the primary bracts are approximately 12 cm. Primary bracts: Lowest approximately 10–12 cm and those near the top are approximately 6 cm.

*Width.*—Scape bracts are approximately 2 cm and the primary bracts approximately 2 to 2.5 cm.

*Number.*—Primary bracts: approximately 16–20. Scape bracts: approximately 8.

*General shape.*—Lanceolate.

*Texture.*—Smooth.

*Margin.*—Entire.

*Color.*—Primary bracts: R.H.S. 160B–160C. Primary bract-ends: R.H.S. 147A.

IV. Flowers:

*Borne.*—Erect on stalks, length of inflorescence being approximately 12–16 cm and width is approximately 18 cm.

*Shape of inflorescence.*—Head.

*Individual; petals.*—Length: Approximately 3 cm. Width: Approximately 0.5 cm. Quantity: Approximately 28 flowers, depending on the size of the plant.

*Color of petals.*—R.H.S. 7a.

*Time of blooming.*—In a fully grown plant flowers can bloom the whole year starting approximately 15 weeks after acetylene treatment or natural induction.

*Duration of blooms.*—Each flower blooms 1 day and the total duration of blooming is about 4 weeks.

V. Reproductive organs:

*Ovaries.*—Superior.

*Stamens.*—6 in number.

VI. Seed characteristics.—Sterile hybrid therefore no fruit or seed.

We claim:

1. A plant of a new and distinct cultivar of Guzmania plant named Pax, as illustrated and described.

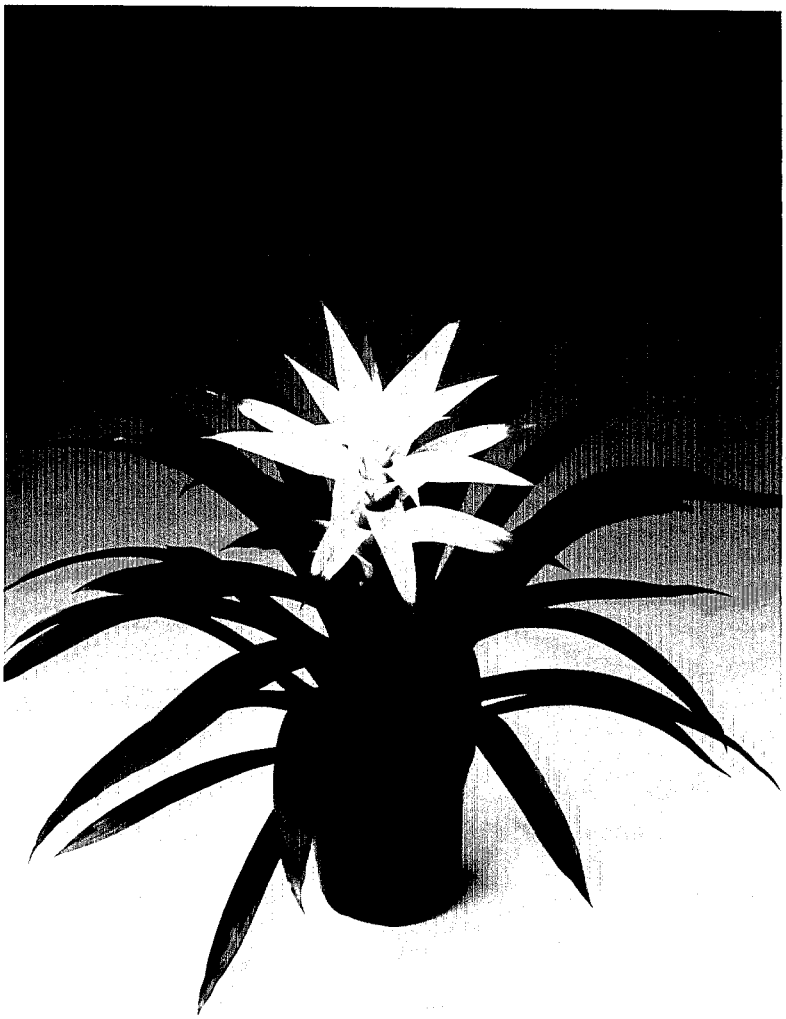

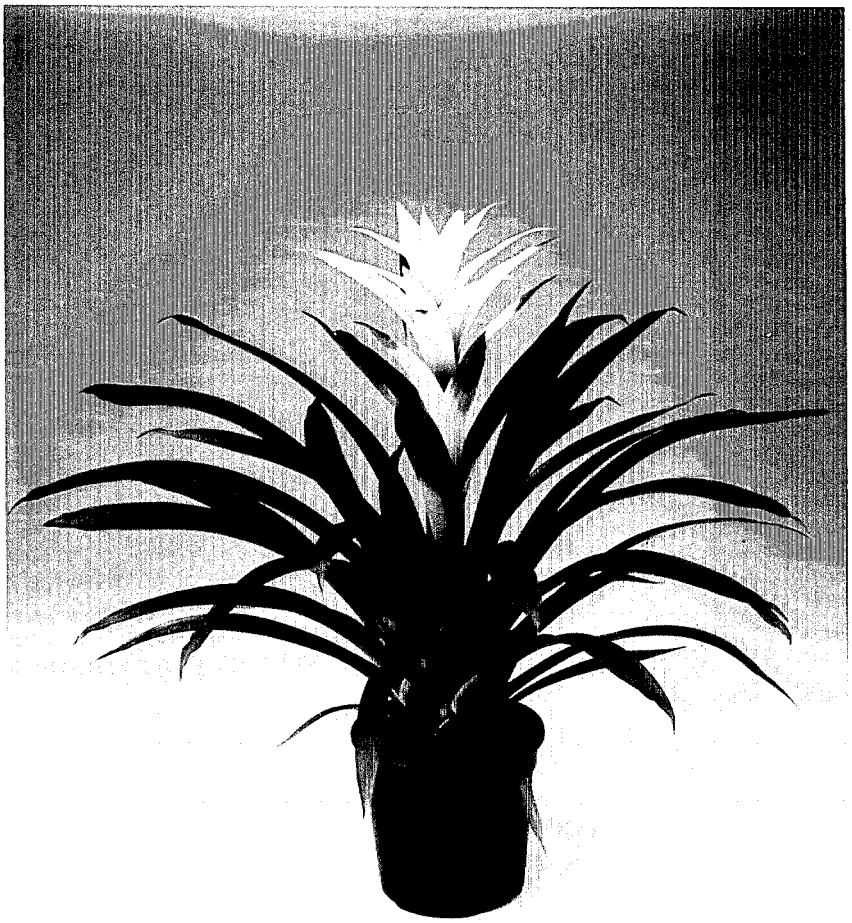

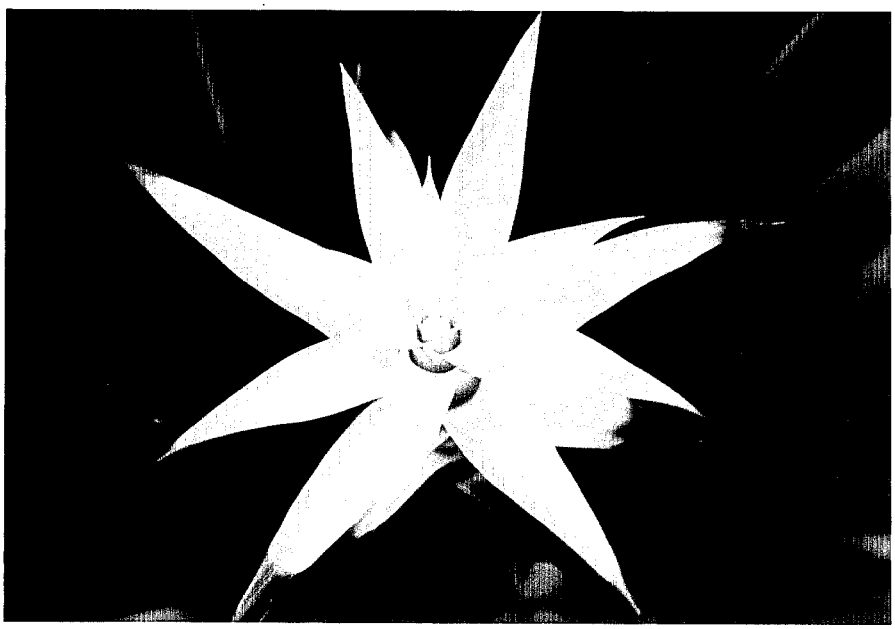

* * * * *